United States Patent [19]
Anderson

[11] 3,967,197
[45] June 29, 1976

[54] METHOD FOR DETECTING MOISTURE IN MULTIPLE LAYER ROOFS

[75] Inventor: Richard G. Anderson, Appleton, Wis.

[73] Assignee: A-Tech, Inc., Appleton, Wis.

[22] Filed: Oct. 4, 1974

[21] Appl. No.: 512,362

[52] U.S. Cl. .............................................. 324/61 R
[51] Int. Cl.² ........................................ G01R 27/26
[58] Field of Search ............ 324/61 R, 61 P, 61 QS, 324/61 QL

[56] References Cited
UNITED STATES PATENTS

| | | | |
|---|---|---|---|
| 1,984,166 | 12/1934 | Walter | 324/61 R |
| 2,123,812 | 7/1938 | Stevens et al. | 324/61 QL |
| 2,529,846 | 11/1950 | McBrayer et al. | 324/61 QS |
| 3,348,140 | 10/1967 | Godding | 324/61 R |
| 3,525,935 | 8/1970 | Cho | 324/61 R |
| 3,713,966 | 1/1973 | Lippke | 324/61 R |

FOREIGN PATENTS OR APPLICATIONS

| | | | |
|---|---|---|---|
| 772,049 | 4/1957 | United Kingdom | 324/61 |

OTHER PUBLICATIONS

Gammie Nuclear Service Co., Advertisement, Cited by Applicant, Gammie Nuclear Service Co., Franklin Park, Ill.
Armm Insulvision Advertisement, Armm consultants.
Kirkwood, Jr., et al. "Measurement of Dielectric Constant & Dissipation Factor of Raw Cottons," Textile Research Jr., vol. 24, 9-1954, pp. 841-847.
Slocombe et al., "Fast Web Moisture Measurement by Electronic Scanning, Tappi, vol. 52, 2-1969, pp. 276-278.

*Primary Examiner*—John K. Corbin
*Assistant Examiner*—Wm. H. Punter
*Attorney, Agent, or Firm*—Theodore J. Long; John M. Winter; Harry C. Engstrom

[57] ABSTRACT

A method for detecting the presence, location, and concentration of moisture in multiple layer built-up roofs. A plurality of spaced points are first marked and located on the roof to be tested. The relative dielectric constant of the roof at each of the spaced points is then measured, the measurements are recorded, and each measurement is associated with the location of the point at which the measurement was taken. The magnitude of the relative dielectric constant of the roof is proportional to the relative concentration of moisture in the roof covering, thus allowing the points at wet portions of the roof to be distinguished from points at dry portions of the roof. Statistical methods may be employed to better separate the measurements taken at dry points on the roof from measurements close in magnitude which are taken at wet points on the roof.

6 Claims, 4 Drawing Figures

METHOD FOR DETECTING MOISTURE IN MULTIPLE LAYER ROOFS

BACKGROUND OF THE INVENTION

1. Field of the Invention

This invention pertains to methods for detecting the presence, location, and concentration of moisture in roof coverings.

2. Description of the Prior Art

Large industrial and commercial buildings often have flat roofs which require a covering for protection from the elements. This covering often consists of multiple layers of tarpaper or felt which are bonded together, usually by covering each layer with hot tar or bitumen before emplacement of another layer. A layer of heat insulating material is commonly provided between the structural roof and the multiple felt layers.

Over a period of time, natural weathering forces result in a deterioration of the integrity of the roof covering. Alternate heating and cooling of the roof causes cracks to appear in the tarpaper or felt. Moisture seeps between the layers and expands by freezing during the winter and evaporation during the summer, with consequent further separation and cracking of the layers. Eventually the covering deteriorates to the point that water leaks into the insulation and through the roof, necessitating replacement of the damaged portion of the covering.

For purposes of convenience in illustration, the deterioration of multiple layer roofs in wet areas may be classified as first stage penetration, second stage penetration, and extensive water penetration or third stage penetration. First stage penetration is the initial phase of water penetration into the roof. The top layers of felt may be somewhat porous from asphalt and tar breakdown from normal weathering, or water may be found between two layers arriving by capillary action from a surface imperfection. There are no leaks into the building at this stage of deterioration, but roof damage may continue at a rapid rate unless the situation is corrected and water entry points sealed. Second stage penetration is similar to first stage penetration except that deterioration has progressed into the lower layers of roofing felts. Water may now be sandwiched between three or four felt layers instead of just the top two as in first stage penetration. While there still may be no water leakage into the building at the second stage, the protective layers of the roof are in very bad shape and leakage into the building can be expected at any time. The felt-bitumen layers must be replaced. The insulation layer in most cases can be salvaged, but should be inspected to determine its condition. At the third or extensive water penetration stage, water has penetrated all the protective felt layers and the insulation as well. Since the binders used in most insulation are water soluble, the roof water often dissolves the binders, and the insulation deteriorates and becomes mushy and also looses its heat insulation ability. In this third stage of extensive water penetration, both the felt layers and the underlying insulation are soaked, and the entire roof covering must be removed and rebuilt from the structural roof on up using new materials.

In general, first stage penetration areas can be most easily repaired by top-coating with a cold applied roofing mastic or an elastomeric coating material. If the penetration is indicated as coming from a flashing crack or tear, the repair should be made with an elastomeric material applied over a polyethylene mesh tape. Asbestos filled bitumastic materials work for temporary repairs. These are not satisfactory for long-term repairs because they become brittle and cracked to again allow water entry.

Second stage penetration indicates much more severe roof deterioration. Only temporary repairs can be made with the top layers. Permanent corrective repairs for second stage penetration areas requires the removal of existing felt plys down to the insulation to completely remove all trapped water. Where visual inspection indicates excessive deterioration of the insulation, it should be removed. The roof should be rebuilt from the insulation on up, or as required from the decking on up, using standard roofing techniques and new dry materials. Hot tar and hot asphalt felt laminates are satisfactory here because all roof water has been removed. Hot roofing materials do not work well over areas in a roof containing moisture, and therefore should not be used in these areas. The repair areas are built up to the level of the existing older built up roofing, and properly overlapped. Cold process roof mastics or elastomeric coatings are applied as a final protective top coat.

Generally, roof covering does not deteriorate over an entire roof at once, and repair or replacement of the entire covering is not justified. However, it may be difficult to define the areas of the covering that need repair or replacement, since water may travel a considerable distance between the layers to the point where the leak in the roof appears. The traditional method of determining areas of wetness in roof coverings has been to take core samples of the covering. This method is time consuming and has the obvious disadvantage of risking destruction of sound roof covering if too great an area is tested, while deteriorated covering far from the point of leakage may be missed if extensive samples are not taken. Moreover, core sampling is an impractical method for detecting the first stages of roof deterioration, which as noted above can often be repaired without replacement of the covering.

Several non-destructive roof wetness testing techniques have been developed in an attempt to reduce the time and expense of testing roofs. These techniques include infrared scanning of roofs to detect cool moist areas, and nuclear particle bombardment to determine hydrogen ion count in the roof covering. Such techniques generally require expensive and delicate equipment, and do not discriminate the first stage and second stage penetration wet areas from dry areas with as high a degree of accuracy as is desirable.

SUMMARY OF THE INVENTION

I have invented a new method for detecting the presence of moisture in a multiple layer built up roof, and for determining the location and the relative concentration of this moisture in the roof. My method is capable of distinguishing the areas of first stage, second stage, and third stage moisture penetration into the roofs, thus facilitating the most efficient and economical repair of the roof. The method does not require the use of complicated equipment, or highly skilled operators, yet the relative concentration of moisture in the roof is measured to a high degree of accuracy.

In applying my method, a number of spaced points are first established on the area of the roof to be tested. These points may be located by laying out a number of spaced lateral and longitudinal intersecting grid lines.

The intersection points of the grid lines form positions in a matrix, each intersection point on the roof being locatable as a position in the matrix. For convenience the matrix may be reproduced in scaled down form on a sheet of paper prepared by the operator. I have found that the moisture concentration in built-up roofs is proportional to the dielectric constant of the roofing material. Thus, by measuring the dielectric constant at each of the grid line intersection points, it is possible to determine the relative concentration of moisture in the roof at the various points spaced over the area of the roof. It is not necessary to measure the absolute dielectric constant of the roof, since it is the relative concentration of moisture in the wet portions of the roof as compared to the dry portions of the roof that is most significant. I have found that the relative dielectric constant of the roof may be effectively measured using a spray field capacitance meter, in which the plates of the capacitor are co-planar. The measurements so obtained are recorded and are associated with the point in the matrix from which they were taken.

In applying my method, the measurements obtained from portions of the roof having first stage penetration may be quite close in magnitude to the normal scatter of readings from the dry roof portions. The measurements indicating first stage penetration may be separated from the dry portion measurements by several techniques, including taking core samples at a number of the spaced points on the roof and examining the core samples to determine if they are from wet or dry portions of the roof. The smallest reading obtained at points having wet core samples can be used to designate all points having measurements higher than such smallest measurement as wet points. Similarly, all points having measurements smaller than the largest measurement at a dry point can be designated as dry points on the roof. Since most multiple layer roofs are similar in construction, and thus have similar dielectric constant properties, it is also possible to use the measurements obtained from a second roof which is known to have wet portions and dry portions, as a standard against which the measurements obtained from the roof being tested can be compared.

Further objects, features and advantages of my invention will be apparent from the following detailed description taken in conjunction with the accompanying drawings showing a preferred method for detecting moisture in multiple layer roofs exemplifying the principles of my invention.

DESCRIPTION OF A PREFERRED EMBODIMENT

Figure 1:
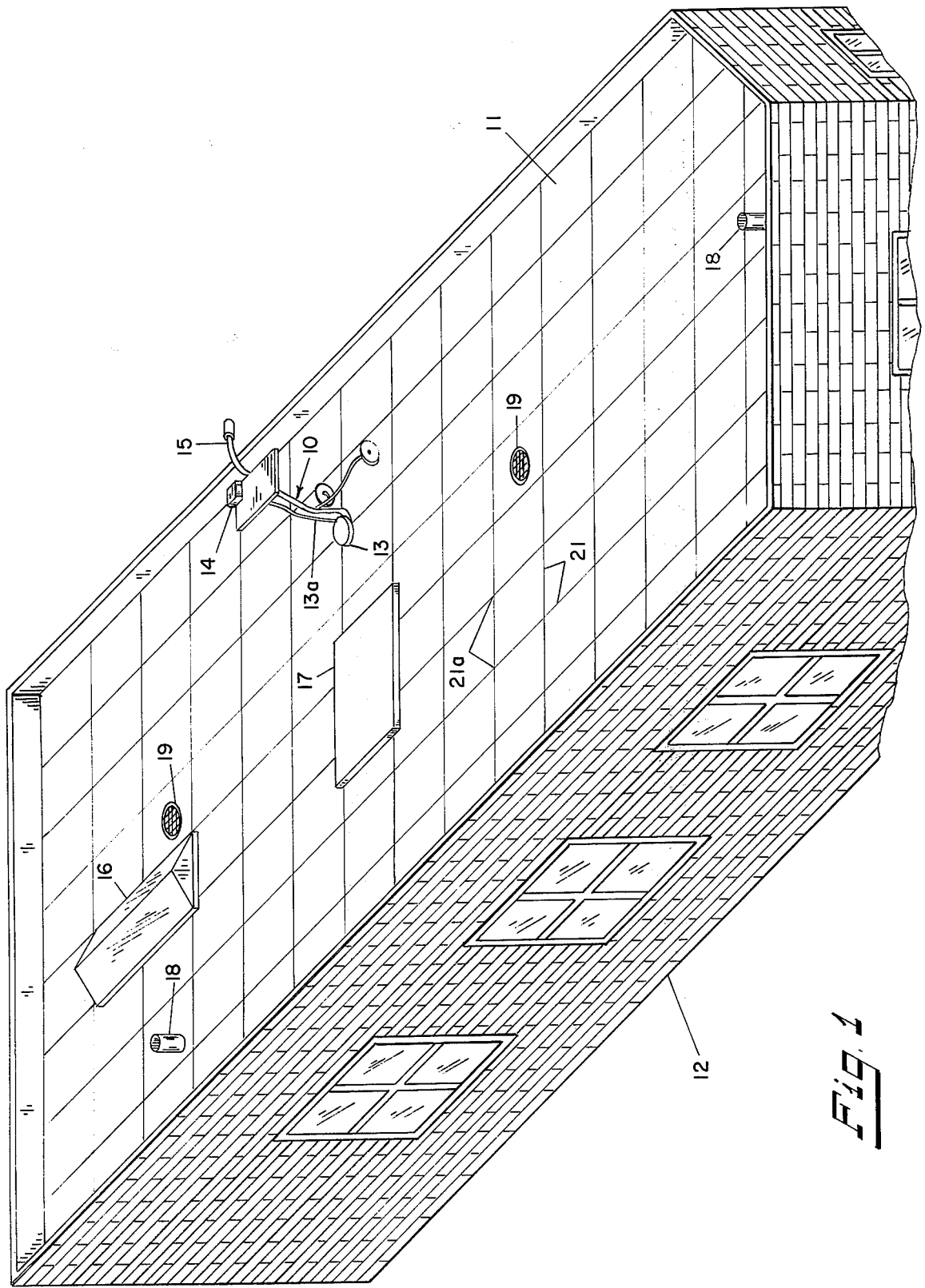
FIG. 1 is a perspective view of a building having a multiple layer roof with a roof capacitance measuring unit in position to take measurements thereon.

Referring now more particularly to the drawings, wherein like numerals refer to like parts throughout the several views, a roof capacitance measuring unit used in my method for detecting moisture in multiple layer built-up roofs is shown generally at 10 in FIG. 1. The capacitance measuring unit 10 is shown in FIG. 1 on the substantially flat roof 11 of a building 12 such as an industrial plant or commercial facility. The capacitance measuring unit consists of a capacitance meter 13 electrically connected by a cord 13a to an ammeter reading dial unit 14, both of which are mounted for convenience on a wheeled cart 15.

Figure 3:
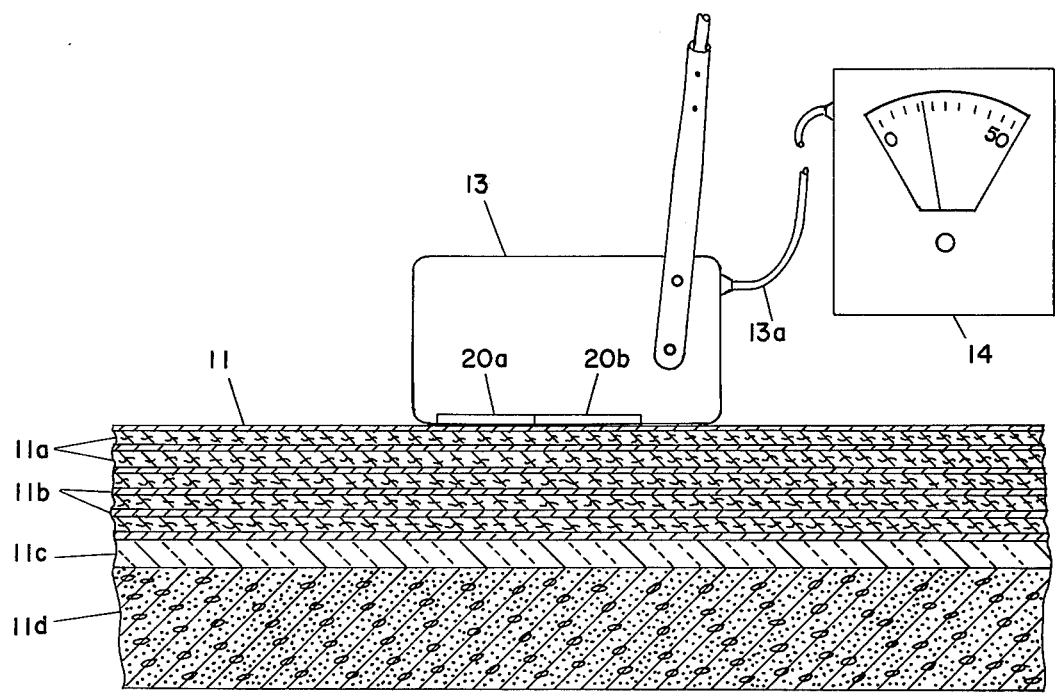
FIG. 3 is a cross sectional view of the roof of the building in FIG. 1, with a capacitance meter in position thereon to take relative capacitance-relative dielectric constant measurements.

Referring to FIG. 3 the capacitance meter 13 is shown in operating position on a cross section of the roof 11. For illustrative purposes, the roof 11 is shown as having a smooth surface. However, the presence of gravel, pebbles, etc., on the surface of the roof does not affect the application of my method. The roof 11 is composed of multiple layers of felt or tar paper 11a which are bonded together by an adhesive layer 11b, this adhesive usually being bitumen or tar. The layers of felt 11a and tar 11b are layed over an insulation layer 11c which is on the structural roof 11d of the building 12. The structural roof 11d is shown for illustrative purposes in FIG. 3 as composed of concrete, but my capacitance method for detecting moisture can also be used with roofs having any other structural material such as steel or aluminum. Although a conductive structural decking may increase meter readings, the increase in readings is substantially uniform in the range of readings near the dry roof portion readings, so that wet areas will still yield relatively higher readings as compared to the dry areas. As described above, the layers of felt 11a are capable of absorbing water where cracks or separations have occurred in the felt and tar layers. Water may also accumulate between layers, causing further layer separation because of freezing and evaporation forces. As a result, water will seep through the protective layers of felt and tar to the insulation layer 11c and will probably leak through the structural roof 11d, which usually is not constructed so as to be water-tight. In addition, there are various openings in the structural roof such as the skylight 16, roof access opening 17, plumbing vents 18, and drains 19 as shown on the roof 11 in FIG. 1. The presence and relative concentration of moisture absorbed by the felt or insulation, or between the layers is detected by the capacitance meter 13 as explained below. It is important that the relative concentration of moisture in the layers be determined because those areas of the roof which have first or second stage moisture penetration may need to be replaced or repaired even though not presently visibly cracked.

The capacitance meter 13 preferably utilizes two coplaner electrodes 20a and 20b which are mounted at the bottom of the meter 13. These electrodes are electrically isolated from one another, and are connected to a source of constant frequency alternating current (AC) power. A spray or fringe electro-static field will exist between the two electrodes and they will in effect form two plates of a capacitor, with a small amount of electric current flowing through the capacitor. This current will be measured by the ammeter reading dial unit 14. The amount of current flowing in the circuit will be proportional to the capacitance of the two electrodes 20a and 20b, which is in turn proportional to the dielectric constant of whatever material is in the spray field between these two electrodes. By definition, a dielectric material between the plates of a capacitor increases the capacitance thereof over the in-vacuum capacitance by multiplying the in-vacuum capacitance by the dielectric constant of the material. I have found that the dielectric constant of the felt and tar layers in a built-up roof increases with an increase in the concentration of moisture in the layers and between the layers. Thus, it is possible to obtain a reading of the relative dielectric constant and hence the relative concentration of moisture in the roof layers by placing the electrodes 20a and 20b of the capacitance meter 13 against the roof surface or against the gravel or pebbles on the surface, and reading on the reading dial unit 14 the current that is flowing in the circuit.

It is to be expected that the dielectric properties of roofing material will vary from building to building, and from point to point on the roof of a single building. These variations can occur because of differences in the material itself, in the number of layers of material that have been placed on the building, in the thickness of the roof layers and the gravel layer, separation of the layers, variations in surface temperature, and so forth, including as one variable the relative concentration of moisture contained within the layers of roofing material. In addition, where water is trapped or absorbed only in a single layer or in very deep layers of roofing material, the readings that are obtained may not vary greatly from the normal scatter of readings obtained from dry roof portions. However, the presence of moisture in a single layer or in deep layers must be ascertained since the roofing will eventually begin to deteriorate in these areas. It is possible, by using my method, to discriminate between the dry portions of the roof and the wet portions where first or second stage moisture penetration has occurred, as will be developed below.

Figure 2:
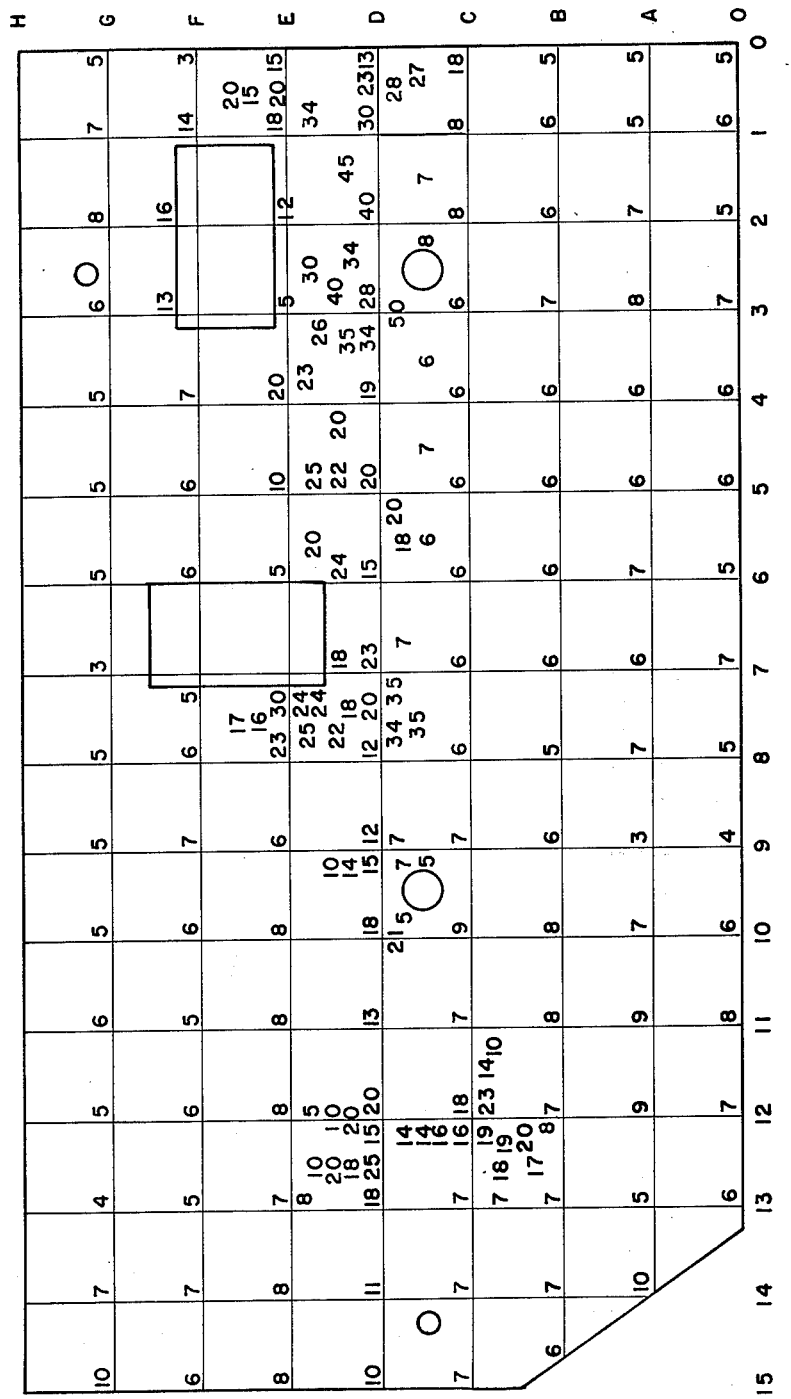
FIG. 2 is a scaled drawing of the roof of the building shown in FIG. 1.

In applying my method of detecting moisture in roofs, the roof 11 to be measured is first marked off into a grid or matrix which preferably has uniformly spaced intersection points at the corners of grid squares that are approximately 5 feet on a side. The lateral and longitudinal intersecting grid lines 21, as shown in FIG. 1, may be physically marked on the roof 11 of the building by chalking the lines on the building or by marking them off with tape, or by merely marking the intersection points 21a of the gridlines. A scaled drawing of the roof 11 with the gridlines 21, as shown in FIG. 2, is then made. Each gridline intersection point is located by assigning the point a lateral and longitudinal position in the matrix, as (0,0), (A,1), (B,5), etc. in the manner shown in FIG. 2. The measuring unit 10 is then placed on the roof 11 and the capacitance meter 13 is calibrated to a convenient value with the capacitance meter in the air away from any dielectric material. Thus the measuring unit will not measure the absolute dielectric constant of the roof covering, but will read the dielectric constant relative to air, or for that matter, relative to any other convenient material. Air provides the most convenient reference material, since its dielectric properties are fairly constant and close to that of a vacuum, and it is available anywhere. The operator then pushes the measuring unit 10 along the gridlines 21 and stops to take relative capacitance or relative dielectric constant measurements with the meter 13 at each gridline intersection point 21a. He marks down the value of the relative dielectric constant reading as shown on the reading dial unit 14 on the scaled drawing shown in FIG. 2, with each reading being marked next to the intersection point 21a which is associated with that reading. Alternatively, the drawing of the roof 11 with the gridlines 21, as shown in FIG. 2, may be prepared initially from measurements taken of the dimensions of the roof. The actual readings with the measuring unit 10 may then be made by pushing the unit along a straight line and taking measurements every 5 feet, and continuing this pattern back and forth across the roof until readings have been taken over the entire roof. A 5 foot square grid has been chosen from experience as yielding the maximum probability of detecting wet areas of the roof, while minimizing the amount of work required to take measurements over the entire roof area.

Figure 4:
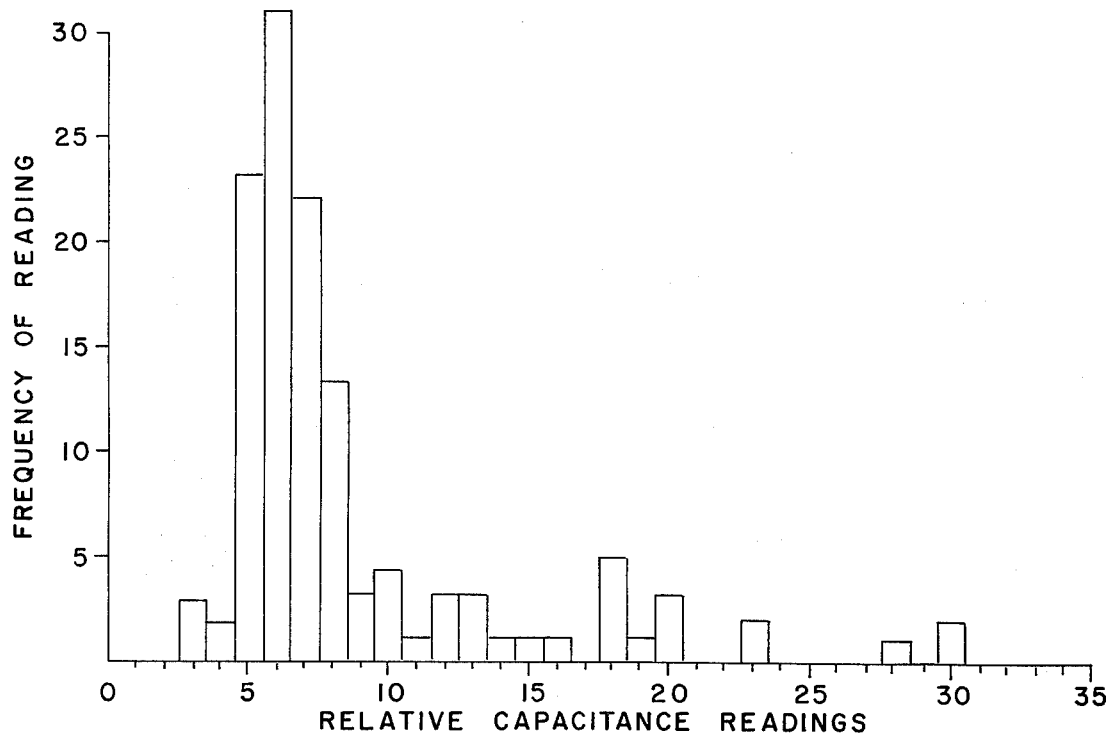
FIG. 4 is a graph showing the frequency of the relative capacitance readings taken on the roof of the building shown in FIG. 1.

The readings which, for illustrative purposes, have been marked to the upper right of the intersection points of the gridlines on the drawing in FIG. 2, were obtained with a particular model of capacitance meter 13 calibrated to a particular reading in air, wherein a capacitance reading in air would be approximately "0". The relative capacitance readings marked on the drawing in FIG. 2 are collected and shown in graphic form in the bargraph of FIG. 4. As shown in FIG. 4, the relative capacitance readings tend to cluster around a reading of 5 or 6, with only scattered readings occurring out at higher values. It has been found that with the particular model of capacitance meter 13 calibrated in air as above, that dry roofs generally tend to read between 3 or 4 and 6 or 7. It has also been found that the standard deviation of readings taken on dry roofs seldom exceeds 1 or 2 where the meter 13 is similarly calibrated in air. Hence, readings of more than 12 or 13 are almost surely not readings taken at dry portions of the roof. The mean and standard deviation of all readings excluding those readings over 13 can then be calculated. The standard formulas for the sample mean M and sample variance $S^2$ are, of course, $$M = \frac{1}{n} \sum_{i=1}^{n} x_i \text{ and } S^2 = \frac{1}{n-1} \sum_{i=1}^{n} (x_i - M)^2,$$

where $x_i$ is the value of reading $i$. The sample mean and sample standard deviations so calculated are considered the estimators of the mean and standard deviation of the population samples from dry portions of the particular roof being measured. There is thus a high probability that any reading that exceeds the dry roof mean plus 3 dry roof standard deviations is a reading taken at a portion of the roof that is wet. Readings beyond 14 or 15 can be conclusively assumed to be at wet portions of the roof. For the readings shown in FIG. 2, the dry roof sample mean is equal to 6.75 and the dry roof sample standard deviation is equal to 2.135, and thus the sum of the sample mean and three times the sample standard deviation is 13.155, which agrees with the original estimate.

The concentration of water in the layers can vary greatly, and water may be contained in one of the deep layers but not in the upper layers, or in fact in more than one layer. The readings taken at wet areas of the roof will thus tend to vary greatly and will not cluster around a single value, but rather will cluster around several reading values. The reason for such clustering can be seen from an examination of Tables 1–5 below.

Table 1

Effect of Layer Position on Meter Readings for one Wet Felt Layer and Dry Insulation (Meter reading on dry insulation = 3.0)

| Number of Felt Layers | Dry Felt | Wet Bottom Felt | Wet Felt Second From Bottom | Wet Felt Third From Bottom | Wet Felt Fourth From Bottom |
|---|---|---|---|---|---|
| 1 | 3.5 | 7.8 | | | |
| 2 | 4.0 | 7.8 | 7.8 | | |
| 3 | 4.3 | 7.7 | 7.6 | 7.8 | |
| 4 | 4.5 | 7.7 | 8.0 | 8.9 | 8.1 |
| 5 | 4.6 | 7.7 | 8.0 | 8.0 | 8.2 |

Table 2

Effect of Layer Position of Meter Readings for two Wet Felt Layers and Dry Insulation (Meter Reading on dry insulation = 3.0)

| Number of Felt Layers | Dry Felt | Wet Bottom Two Felts | Wet Felt Second and Third from Bottom | Wet Felt Third and Fourth from Bottom | Wet Felt Fourth and Fifth from Bottom |
|---|---|---|---|---|---|
| 1 | 3.5 | | | | |
| 2 | 4.0 | 11.0 | | | |
| 3 | 4.3 | 10.5 | 11.0 | | |
| 4 | 4.5 | 10.4 | 10.6 | 11.4 | |
| 5 | 4.6 | 10.0 | 10.3 | 10.9 | 10.5 |

Table 3

Effect of Layer Position on Meter Readings for three Wet Felt Layers and Dry Insulation (Meter Reading on dry insulation = 3.0)

| Number of Felt Layers | Dry Felt | Wet Bottom Three Felts | Wet Felts Second Third and Fourth from Bottom |
|---|---|---|---|
| 1 | 3.5 | | |
| 2 | 4.0 | | |
| 3 | 4.3 | 13.0 | |
| 4 | 4.5 | 12.1 | 11.4 |
| 5 | 4.6 | 11.6 | 10.5 |

Table 4

Effect of the Number of Wet Felt Layers on Dry Insulation (Meter reading on dry insulation = 3.0)

| Number of Wet Felt Layers | Meter Reading |
|---|---|
| 1 | 8.0 |
| 2 | 11.0 |
| 3 | 12.5 |
| 4 | 13.0 |
| 5 | 13.1 |

Table 5

Effect of the Number of Wet Felt Layers on Wet Insulation (Meter reading on dry insulation = 3.0)

| Number of Wet Felt Layers | Meter Reading |
|---|---|
| 0 | 16.0 |
| 1 | 18.0 |
| 2 | 19.5 |
| 3 | 20.1 |
| 4 | 21.0 |
| 5 | 21.5 |

Where one felt only is wet, the meter readings (relative dielectric constant measurements) tend to cluster around 8.0, as shown in Table 1. Where two or more felts are wet, the meter readings tend to remain within the range from 10.0 to 13.0, as shown in Tables 2–4. Large meter readings of 16.0 or more are obtained when the insulation layer is wet, as demonstrated in Table 5. It is thus seen that for the type of roof being tested here, readings clustered around 8.0 indicate stage one penetration, readings within the range of 10.0 to 13.0 indicate stage two penetration, and readings over 16.0 indicate stage three penetration.

Thus it would be difficult, if not impossible, to estimate the sample mean and sample standard deviation of only the population of readings from wet portions of the roof that are close to the dry roof portion readings. Certainly the parent population of all wet roof portions would not be normal, since the population obviously has several modes. It is, of course, desirable to ascertain as many of the wet roof points as possible without including therein, as error, an unreasonable number of dry roofing points. It may be assumed here that the dry roof readings are taken from a population that is approximately normal, which corresponds to previous experience. The mean of this population can be estimated by the sample mean M of 6.75, and the population standard deviation can be estimated by the sample standard deviation S of 2.135. If such a normal population is assumed, only 10% of the dry roof readings should be greater than 9.5 and only 5% of the dry roof readings should be greater than 10.27. Thus, if all of the readings which are greater than 9 are considered to be wet roof readings, at a maximum it is to be expected that only 10% of the actual dry roof readings would be mistaken for wet roof readings.

This error estimation method can be generalized to reduce the maximum probability of error (i.e. designating a dry point on the roof as a wet point) below any desired probability P. The relative dielectric constant measurements taken at several points which are at wet portions of the roof are first determined. This may be done in several ways, including taking core samples at several of the spaced grid intersection points and determining from inspection of the core samples whether they are from wet portions of the roof. Where a wet core is found, that grid intersection point from which the core is taken is designated as a point at a wet portion of the roof. A second method of determining several wet points utilizes the experience gained from measurements on other roofs having similar construction to the roof being tested. Construction of two roofs is similar if both roofs have coverings having substantially the same number of layers of the same or similar material. Most multiple layer roofs have at least four layers of felt and bitumen over insulation and are thus substantially similar, although the construction of the underlying structural roof may vary. However, as indicated previously, a conductive structural roof may add a substantially uniform increase in readings to both dry and wet roof readings in the range near the dry roof readings, and thus the effect of the structural roof can be compensated for. As demonstrated in Tables 1–5 for the particular roof being tested there, with the dry roof readings tending to cluster around a reading of 5.0, wet roof readings should begin at a reading of 8.0, and the roof is almost certainly wet where readings of 10.0 and above are obtained. Thus, on a roof similar to that for which the test results are shown in Tables 1–5, relative dielectric constant measurements greater than 10.0 are almost certainly taken from wet portions of the roof and may be designated as such.

The sample mean M and sample standard deviation S are then calculated for all relative dielectric constant measurements which are less than any measurement obtained from the points that have previously been determined to be at wet portions of the roof. The parent population of dry portion measurements is estimated as having a normal probability distribution with estimated mean M and estimated variance $S^2$. The actual mean and variance of the parent population will very likely be less than M and $S^2$ respectively, since only measurements which were almost certainly taken from wet portions of the roof were excluded from the calculation of M and $S^2$, whereas it is quite likely that some high measurements taken from wet portions of the roof were included in the calculations.

For a random variable having a normal probability distribution of mean M and variance $S^2$, there is a number K such that there is less than a probability P that the random variable is greater than or equal to K. Given M, $S^2$, and P, the number K can be calculated from tables of the standard normal distribution, using conventional techniques. For the numerical example given above, where P=0.1, M=6.75, and S=2.135, K is found to be 9.5. Thus, any points on the roof having relative dielectric constant measurements which are greater than K can be designated as points from wet portions of the roof with less than a probability P of designating a dry point as a wet point.

In order to obtain readings that are even more accurate, it may be desirable to take readings on a day that has followed several days of dry weather to establish a good baseline for dry roof readings. It would than be desirable to take readings again after a heavy rain, or, if this is inconvenient, to irrigate the roof over a period of a day or so to insure that any wet areas, or areas that are susceptible to wetness, will have become thoroughly wetted.

After measurements have been taken of the relative dielectric constant at each of the spaced grid intersection points, the general areas of the roof where there is moisture in the roof covering are known. However, it is often desirable to obtain a more precise outline of the wet areas than that provided by the grid intersection points. Thus, a relative dielectric constant measurement can be taken at at least one point which is between a wet point and an adjoining dry point. If the measurement shows that the point is dry, that point can be designated as an outer limit of the wet area. If the point is wet, another measurement may be made between that point and an adjoining dry point to better define the limits of the wet areas.

It is also desirable to obtain a more precise moisture profile of the wet areas between the points designated as at wet portions of the roof. Relative dielectric constant measurements may thus be taken at at least one point between adjoining wet points. Several of these measurements between wet points are shown for illustrative purposes in FIG. 2. This expanded moisture profile allows a determination to be made of those wet portions of the roof having first stage penetration, second stage penetration, and third stage penetration, in accordance with the magnitudes of the relative dielectric constant measurements. The nature of the repairs required on the roof in the wet portions can thus be determined.

It is understood that my invention is not confined to the particular methods herein illustrated and described, but embraces all such modified forms thereof as may come within the scope of the following claims.

I claim:

1. A method of detecting the presence and location of moisture in a multiple layer roof with less than a chosen probability P of designating a point at a dry portion of the roof as a point at a wet portion of the roof, comprising the steps of:
   a. locating a plurality of spaced points over the area of the roof,
   b. measuring the relative dielectric constant of the roof at each of said spaced points,
   c. recording the relative dielectric constant measurements obtained at each of said spaced points and associating each measurement with the location of the point at which it was taken,
   d. locating a plurality of said spaced points which are at wet portions of the roof,
   e. calculating the sample mean M of all of said relative dielectric constant measurements which are less than any measurement obtained from said plurality of points which are located at wet portions of the roof,
   f. calculating the sample standard deviation S of all of said relative dielectric constant measurements which are less than any measurement obtained from said plurality of points which are located at wet portions of the roof;
   g. calculating a number K such that for a random variable having a normal probability distribution of mean M and variance $S^2$, there is less than a probability P that the random variable will be greater than or equal to K, and
   h. designating as points at wet portions of the roof those points on the roof having relative dielectric constant measurements that are greater than K.

2. The method as specified in claim 1 wherein the relative dielectric constant at each of said spaced points is measured with a spray field capacitance meter.

3. The method as specified in claim 1 wherein the step of locating a plurality of said spaced points which are at wet portions of the roof comprises taking core samples of the roof at a plurality of said spaced points, examining the core samples to determine if they are from wet or dry portions of the roof, and designating as wet points those points on the roof where the core samples taken therefrom are determined to be from wet portions of the roof.

4. The method as specified in claim 1 wherein the step of locating a plurality of said spaced points which are at wet portions of the roof comprises taking relative dielectric constant measurements at a plurality of spaced points on a second multiple layer roof which is similar in construction to the roof being tested, recording said measurements taken at points which are known to be at wet portions of the second roof, and designating as wet points on the roof being tested any points having relative dielectric constant measurements which are greater than or equal to the smallest dielectric constant measurement taken at said points which are known to be at wet portions of the second roof.

5. A method of detecting the presence and location of moisture in a multiple layer roof comprising the steps of:
 a. locating a plurality of spaced points over the area of the roof;
 b. measuring the relative dielectric constant of the roof at each of said spaced points;
 c. recording the relative dielectric constant measurements obtained at each of said spaced points and associating each measurement with the location of the point at which it was taken;
 d. locating a plurality of said spaced points which are at dry portions of the roof by taking relative dielectric constant measurements at a plurality of spaced points on a second multiple layer roof which is substantially similar in construction to the roof being tested and which is known to be substantially dry, calculating the sample mean and sample standard deviation of the relative dielectric constant measurements taken on said second multiple layer roof, and designating as dry points on the roof being tested any points having relative dielectric constant measurements which are less than the sum of said second roof sample mean plus three times said second roof sample standard deviation;
 e. comparing the relative dielectric constant measurements taken at said spaced points over the area of the roof with those measurements taken at said points which are located at dry portions of the roof; and
 f. designating as wet points those points on the roof having relative dielectric constant measurements which are greater than any measurement taken at said points which are at dry portions of the roof.

6. A method of detecting the presence and location of moisture in a multiple layer roof, comprising the steps of:
 a. locating a plurality of spaced points over the area of the roof;
 b. measuring the relative dielectric constant of the roof at each of said spaced points;
 c. recording the relative dielectric constant measurements obtained at each of said spaced points and associating each measurement with the location of the point at which it was taken;
 d. locating a plurality of said spaced points which are at dry portions of the roof;
 e. calculating the sample mean and sample standard deviation of the relative dielectric constant measurements taken at said points which are located at dry portions of the roof;
 f. designating as wet points those points on the roof having relative dielectric constant measurements which are greater than the sum of said dry portion sample mean plus three times said dry portion sample standard deviation.

* * * * *